United States Patent
Nguyen et al.

(10) Patent No.: US 10,339,274 B2
(45) Date of Patent: Jul. 2, 2019

(54) VIRAL NEOEPITOPES AND USES THEREOF

(71) Applicant: NantOmics, LLC, Culver City, CA (US)

(72) Inventors: Andrew Nguyen, San Jose, CA (US); Stephen Charles Benz, Santa Cruz, CA (US); John Zachary Sanborn, Santz Cruz, CA (US)

(73) Assignee: NANTOMICS, LLC, Culver City, CA (US)

( * ) Notice: Subject to any disclaimer, the term of this patent is extended or adjusted under 35 U.S.C. 154(b) by 0 days.

(21) Appl. No.: 15/291,516

(22) Filed: Oct. 12, 2016

(65) Prior Publication Data

US 2017/0032103 A1    Feb. 2, 2017

Related U.S. Application Data

(60) Provisional application No. 62/240,471, filed on Oct. 12, 2015.

(51) Int. Cl.
| | |
|---|---|
| *G16H 20/40* | (2018.01) |
| *G16H 10/40* | (2018.01) |
| *A61K 39/00* | (2006.01) |
| *G06F 19/00* | (2018.01) |
| *G16B 35/00* | (2019.01) |
| *G16C 20/60* | (2019.01) |

(52) U.S. Cl.
CPC ...... *G06F 19/3481* (2013.01); *A61K 39/0011* (2013.01); *G16B 35/00* (2019.02); *G16C 20/60* (2019.02); *G16H 10/40* (2018.01); *A61K 39/00* (2013.01); *G16H 20/40* (2018.01)

(58) Field of Classification Search
None
See application file for complete search history.

(56) References Cited

U.S. PATENT DOCUMENTS

2011/0293637 A1* 12/2011 Hacohen ............ C12Q 1/6886
424/173.1

OTHER PUBLICATIONS

IARC Monographs (2007) VOl 90-Molecular Mechanisms of HPV-induced Carcinogenesis:pp. 432-465.*
Charoentong et al. (Cancer Immunol. Immunother. (2012) vol. 61:1885-1903).*
Schumacher et al. (Nature Apr. 3, 2015; vol. 348, Issue 6230:69-74; see p. 70, col. 1).*
Carreno et al. (Science (2015) 15 Ma7; vol. 348, Issue 6236:803-808).*
Akagi, K., et al., "Genome-wide Analysis of HPV Integration in Human Cancers Reveals Recurrent, Focal Genomic Instability," Genome Research, vol. 24, pp. 185-199, Feb. 2014.
Chapter 4. In IARC Monographs on the Evaluation of Carcinogenic Risk to Humans—Human Papillomaviruses "Molecular Mechanisms of HPV-Induced Carcinogenesis," IARC Monographs, vol. 90, pp. 432-465 (2007).
Schmitz, Martina, et al., "Non-Random Integration of the HPV Genome in Cervical Cancer," PLoS One, vol. 7, Issue 6: pp. 1-10, Jun. 27, 2012.

* cited by examiner

*Primary Examiner* — Lori A. Clow
(74) *Attorney, Agent, or Firm* — Umberg/Zipser, LLP

(57) ABSTRACT

Contemplated antiviral/cancer treatments comprise analysis of neoepitopes from viral DNA that has integrated into the host genome, and design of immunotherapeutic agents against such neoepitopes.

17 Claims, 2 Drawing Sheets
Specification includes a Sequence Listing.

| Entry | Peptide | HLA-A02:01 | HLA-A68:01 | HLA-B44:02 | HLA-B44:03 | HLA-C05:01 | Gene | Variant Affected |
|---|---|---|---|---|---|---|---|---|
| Entry_57 | TLHEYMLDL (SEQ. ID No. 1) | 48 | 32582 | 21214 | 41256 | 31182 | E6 | |
| Entry_107 | YNIVTFCCK (SEQ. ID No. 2) | 25613 | 83 | 23014 | 42543 | 34207 | E6 | |
| Entry_222 | CMSCCRSSR (SEQ. ID No. 3) | 23210 | 210 | 22357 | 46621 | 37693 | E6 | |
| Entry_41 | GTLGIVCPI (SEQ. ID No. 4) | 155 | 23697 | 19473 | 36528 | 33130 | E6 | |
| Entry_49 | YMLDLQPET (SEQ. ID No. 5) | 5 | 29235 | 21414 | 45184 | 28298 | E6 | |
| Entry_70 | KLPQLCTEL (SEQ. ID No. 6) | 87 | 39073 | 23397 | 46114 | 32225 | E6 | KLPDLCTEL (SEQ. ID No. 7) |
| Entry_10 | FYSKISEYR (SEQ. ID No. 8) | 25094 | 15 | 23633 | 45774 | 32437 | E6 | |
| Entry_90 | EVYDFAFRD (SEQ. ID No. 9) | 25824 | 474 | 24091 | 37817 | 36132 | E6 | |
| Entry_207 | LRCINCQK (SEQ. ID No. 10) | 27421 | 296 | 23303 | 48272 | 36914 | E6 | |
| Entry_205 | LLMGTLGIV (SEQ. ID No. 11) | 19 | 32840 | 22284 | 44804 | 25970 | E6 | |
| Entry_26 | IVCPICSQK (SEQ. ID No. 12) | 25749 | 24 | 24070 | 47889 | 34213 | E6 | |
| Entry_239 | QAEPDRAHY (SEQ. ID No. 13) | 30382 | 10724 | 20810 | 40317 | 282 | E6 | |
| Entry_144 | ETTDLYCYE (SEQ. ID No. 14) | 29282 | 304 | 23278 | 43095 | 29379 | E7 | |
| Entry_171 | HLECVYCK (SEQ. ID No. 15) | 4793 | 325 | 22054 | 46284 | 30907 | E7 | |
| Entry_101 | FAFRDLCIV (SEQ. ID No. 16) | 115 | 11288 | 22804 | 43644 | 12933 | E7 | |
| Entry_197 | YAVCDKCLK (SEQ. ID No. 17) | 23811 | 86 | 21380 | 46459 | 24703 | E7 | |
| Entry_94 | TTLEQQYNK (SEQ. ID No. 18) | 21284 | 59 | 22084 | 46846 | 31700 | E7 | |
| Entry_132 | VCDKCLKFY (SEQ. ID No. 19) | 25389 | 35252 | 22163 | 40224 | 137 | E7 | |

Figure 1

| Protein | Peptide | HLA-A02:01 | HLA-A68:01 | HLA-B44:02 | HLA-B44:03 | HLA-C05:01 | Gene |
|---|---|---|---|---|---|---|---|
| Entry_11 | KLPDLCTEL (SEQ. ID No. 20) | 12 | 37790 | 23519 | 45874 | 27220 | E6 |
| Entry_9 | FQDPQERPI (SEQ. ID No. 22) | 1943 | 40164 | 20178 | 40923 | 299 | E6 |

| Gene ID and Position | Variant | Protein Change | Base Change | Normal |
|---|---|---|---|---|
| NP_041325.1-145:146 | Missense | p.Q21D | G->T | KLPQLCTEL (SEQ. ID No. 21) |
| NP_041325.1-132:133 | Missense | p.R17I | G->T | FQDPQERPR (SEQ. ID No. 23) |

Figure 2

VIRAL NEOEPITOPES AND USES THEREOF

This application claims the benefit of priority to U.S. provisional application 62/240,471 filed on Oct. 12, 2015.

FIELD OF THE INVENTION

The field of the invention is treatment of viral and neoplastic diseases, and especially as they relate to immunological treatment of virus-associated diseases.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Human Papilloma Viruses are relatively small DNA viruses that infect various epithelial tissues and can be classified into cutaneous types and mucosotropic types. In addition, Human Papilloma Viruses (HPV) can also be classified as low- and high-risk types, depending on their difference in their ability to promote malignant transformation in infected tissues. For example, HPV types 16 and 18 are mucosotropic HPVs that are associated with more than 99% of cervical carcinomas. In most of these cancers, the viral DNA genome is integrated into the genome of the host. Infection with most HPV types is self-limiting in a significant number of cases. However, persistent infection and neoplastic transformation is observed in a clinically relevant proportion of patients, especially where infection was with a high-risk type HPV.

More recently, vaccine formulations have become available against the most common high-risk HPV types. Unfortunately, vaccinations are generally not effective against an already established infection. Moreover, a vaccination may also be less effective where the virus has undergone sufficient genetic changes. Effective HPV treatment may be further complicated by the concurrent genomic instability, which is generally attributed to interactions of viral proteins E6 and E7 with normal DNA damage response (typically mediated via the hosts p53 and pRb proteins).

Therefore, despite improved treatments and vaccinations, several problems with HPV infection, and especially persistent HPV infection still remain. Thus, there is still a need for systems and methods that improve treatment of HPV infections.

SUMMARY OF THE INVENTION

The inventors have now discovered that omics analysis can be used to verify or increase the efficacy of an immunotherapeutic composition against a pathogen or disease. Preferably, the omics data obtained from a patient are compared to reference omics data for the pathogen and/or disease, and neoepitopes are identified from the patient's omics data that have increased or new binding affinity towards the patient's HLA-type and/or that are lost relative to epitopes otherwise found in the reference omics data for the pathogen and/or disease. Moreover, omics analysis of a pathogen or disease can also be used to guide rational design of neoepitopes expected to bind at high affinity to HLA-type of the patient, and so identified neoepitopes can be expressed/imported into a diseased cell for expression.

Most preferably, all of the omics analysis as well as HLA-typing and HLA-matching is performed in silico using whole genome sequencing data. Moreover, while viral diseases are especially contemplated, other diseases with genetic etiology are also deemed suitable.

It is contemplated that HLA-typing involves high-accuracy variant calling from patient sequence data, especially for HLA-typing using DNA and/or RNA sequences from sequencing machines. In some embodiments determining an HLA-type of a patient involves matching an HLA reference sequence with patient omics data. Omics data can be derived from healthy tissue of the patient, while in preferred embodiments it is derived from diseased tissue. The HLA reference sequence includes a plurality of sequences of known and distinct HLA alleles. The patient omics data comprises a plurality of sequence reads, which preferably can be divided into a plurality of respective sets of k-mers. A composite de Bruijn graph can be generated using the HLA reference sequence and the plurality of respective sets of k-mers.

In preferred embodiments each of the known and distinct HLA alleles are ranked using a composite match score that is calculated by votes. Votes can be tallied for each k-mer that matches a corresponding segment in the known and distinct HLA alleles and used to rank the alleles. The topmost allele in the ranking is identified as a primary HLA-type of the patient, and a re-ranking of remaining alleles with bias against k-mer matching the first HLA-type then provides a secondary HLA-type of the patient.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 depicts exemplary results for binding epitopes and neoepitopes with respect to predicted patient HLA-types.

FIG. 2 depicts information regarding predicted bound neoepitopes with high binding affinity for a patient HLA type.

DETAILED DESCRIPTION

The inventors have now discovered that efficacy of immunotherapeutic compositions can be readily ascertained prior to treatment, and/or that immunotherapeutic compositions can be prepared to particularly target a diseased tissue in a patient and disease-specific manner. Most typically, contemplated compositions, systems, and methods rely on detection of neoepitopes that are associated with a disease or pathogen, where the neoepitope is either acquired and/or artificially introduced. For example, neoepitopes can be acquired by (e.g., retro) viral insertion of DNA into a host genome and attendant change in the genomes of the host and pathogen (e.g., via increased mutation rate or genomic instability after HPV integration), or introduced into a host via targeted integration (e.g., via a CRISPR/Cas9 or CRISPR/Cpf1 cassette) of a recombinant nucleic acid encoding the neoepitope(s). Most preferably, targeted insertion is in or proximal a nucleic acid sequence associated with the pathogen (e.g., virus) or disease (e.g., oncogen).

For example, and in one especially contemplated aspect of the inventive subject matter, a biopsy is taken from a cervical carcinoma or pre-neoplastic lesion (or other virally associated tumor) and whole genomics sequencing is performed to so obtain omics data of the diseased tissue. In addition, exome analysis and/or RNA analysis may be performed to identify expressed genes and/or expression levels. Such may additionally include biopsies from one or more lymph nodes proximal to the tumor, and distant metastases or circulating tumor cells. In addition, it is generally preferred that omics analysis is performed in which omics data are directly compared against patient matched normal tissue (i.e., non-diseased tissue from the same patient) to obtain patient-specific mutational changes.

In most cases, the omics data are obtained from the biopsy samples following standard tissue processing protocol and sequencing protocols. While not limiting to the inventive subject matter, it is typically preferred that the data are patient matched tumor data (e.g., tumor versus same patient normal), and that the data format is in SAM, BAM, GAR, or VCF format. However, non-matched or matched versus other reference (e.g., prior patient normal or prior patient tumor, or homo statisticus) are also deemed suitable for use herein. Therefore, the omics data may be 'fresh' omics data or omics data obtained from a prior procedure (or even different patient).

In still further contemplated aspects, the omics analysis will also employ one or more reference nucleic acid sequences, which may comprise one or more viral sequences (e.g., from a collection of different virus or serotypes as is described in WO2015/048546. Thus, it should be appreciated that omics analysis is not limited to patient native nucleic acid sequences, but that such omics analysis also searches for and identifies non-patient nucleic acid, and most typically pathogen nucleic acid (e.g., parasite, virus, bacterial, fungal, etc.). In another example, it should also be appreciated that the reference nucleic acid may also be a nucleic acid sequence from a prior biopsy, and especially nucleic acid sequence data that includes a prior oncogenic mutation. Thus, reference sequences may also be obtained from the patient, albeit from a different point in time to so allow identification of clonal drift or introduction of new mutations in the tumor that were previously not present or detected.

Viewed from another perspective, it is contemplated that rapid analysis can be achieved by modification of a reference genome (which may be obtained from healthy host tissue or from a non-host tissue) in silico where one or more non-patient genome sequences (and most preferably the entire viral genome) is merged with the reference genome to so form a chimeric reference nucleic acid sequence.

Consequently, the inventors contemplate a method in which an analysis engine is informationally coupled to a sequence database that stores a nucleic acid sequence from a virus-associated tumor and a chimeric reference nucleic acid sequence, wherein the chimeric reference nucleic acid sequence comprises at least one viral nucleic acid sequence and a mammalian nucleic acid sequence. In some embodiments, the chimeric reference nucleic acid sequence alternatively or additionally comprises at least on disease-specific nucleic acid sequence. The analysis engine is then used to identify integration of at least some of the viral nucleic acid sequence in the chimeric reference nucleic acid sequence with an allele in the nucleic acid sequence from the virus-associated tumor.

Suitable reference genomes for use in the chimeric reference nucleic acid sequence include whole genome nucleic acid sequences of the same patient and are typically obtained from non-diseased tissue. For example, a reference genome nucleic acid may be obtained from whole blood, from tissue adjacent to a cancerous tissue, or from a buccal swab or biopsy. Alternatively, the reference genome may also be obtained from a sample taken earlier from the patient, or a previous whole genome sequencing attempt. In still further alternative aspects, the reference genome may also be a genome sequence from the same species (e.g., human or other mammalian), preferably stratified by gender, or an average or consensus sequence for the same species. Most typically, the reference genome will be or encompass the entire genome. However, smaller portions of the genome are also contemplated and include at least one chromosome, or two-five chromosomes, or five-ten chromosomes, or more than ten chromosomes. Alternatively, the reference genome may also be only representative of a portion (e.g., between 1-10%, between 10-30%, between 30-60%, or between 60-90%) of the entire exome or entire transcriptome. Thus, and viewed form yet another perspective, the reference genome will typically include at least 10%, or at least 30%, or at least 50%, or at least 70% of the entire genome of the human (or other species).

Suitable non-patient genomes for use in the chimeric reference nucleic acid sequence include whole genome nucleic acid sequences of at least one virus, and more typically of a collection of viruses with known association with a disease, and especially of tumor-associated viruses (i.e., virus that is known to be associated with a cancerous disease). For example, genome sequences of viruses deemed suitable for use herein include those from HTLV-1 (associated with adult T-cell leukemia), HPV viruses (associated with cervical cancer, skin cancer, head and neck cancer, and anogenital cancers), HHV-8 (associated with Kaposi's sarcoma, primary effusion lymphoma, Castleman's disease), EBV (associated with Burkitt's Lymphoma, nasopharyngeal carcinoma, post-transplant lymphomas, and Hodgkin's disease), HBV and HCV (associated with hepatocellular carcinoma), SV40 (associated with brain cancer, bone cancer, mesothelioma), BKV (associated with prostate cancer), JCV (associated with brain cancer), HERVs (associated with germ cell tumors, breast cancer, ovarian cancer, and melanoma), HMTV (associated with breast cancer), KSHV (associated with Kaposi's Sarcoma), and TTV (associated with gastrointestinal cancer, lung cancer, breast cancer, and myeloma). However, it should be appreciated that suitable viruses also include those that are not currently known for a particular disease association.

On the other hand, virus sequences suitable for use herein may also be stratified by one or more common classifiers, which may include organ specificity (e.g., HBV, HCV), cancer type specificity, or risk-type within a group of viruses. For example, where the virus is an HPV virus, suitable non-patient genome sequences may include those associated with high-risk for cervical or other urogenital cancer, including HPV type 16, 18, 31, 33, 35, 39, 45, 51, 52, 56, 58, 59, 68, 69, 73, and/or 82. Most typically, the non-patient genome will be or encompass the entire genome. However, smaller portions of the genome are also contemplated and include portions of the non-patient genome, for example, one or more single non-patient genes or transcription units, or at least 10%, or at least 30%, or at least 50%, or at least 70% of the entire genome of the virus.

Suitable disease-specific nucleic acid sequences for use in the chimeric reference nucleic acid sequence include at least one disease-specific known neoepitope, splice variation, or chromosomal translocations, and more typically include a collection of disease-specific known neoepitopes, splice variations, or chromosomal translocations. For example, disease-specific known neoepitopes can include those known in the art or identified in available databases such as the Cancer Research Institute's Peptide Database, the Immune Epitope Database, the Cancer Immunome Atlas, etc. It should be appreciated that disease-specific splice variations can include those known in the art or identified in available databases such as Ensembl, TCGA SpliceSeq, etc (e.g., alternative splicing of the KLHDC7B, sycp2, or HMMR genes in cervical carcinoma tissue). It is contemplated that disease-specific chromosomal translocations can include those known in the art or identified in available databases such as the Disease Associated Chromosomal Rearrangements Online, Database of Chromosomal Rearrangements In Diseases, the Mitelman Database, etc (e.g., translocation of 2.3 Mb interval on 11q13 to chromosome 3 in cervical carcinoma tissue).

It is particularly preferred that the chimeric reference nucleic acid sequence will include the non-patient nucleic acid sequence(s) as one or more individual units that are appended to the reference genome nucleic acid sequence. Most typically, the individual units for the respective non-patient nucleic acid sequence will be organized/labeled as individual chromosomes. Among other advantages, it should be noted that using such arrangement (particularly where the sequence comparison is done using incremental synchronous alignment) will allow for rapid identification of the location of the genomic integration, copy number determination, and affected alleles. Therefore, it is also contemplated that the non-patient nucleic acid sequences will be organized in the same format (e.g., BAM, SAM, FASTA, or FASTA index) as the reference genome nucleic acid sequence. However, alternative formats are not expressly excluded. In view of the above, it should thus be recognized that the chromosome count for a chimeric reference nucleic acid sequence for a mammal may significantly exceed the chromosome count for the nucleic acid sequence from the virus-associated tumor. For example, the chromosome count for the chimeric reference nucleic acid sequence may exceed the chromosome count for the nucleic acid sequence from the virus-associated tumor by at least one, at least five, at least ten, at least 20, at least 50, and even more. Indeed, the exact chromosome count will be determined by the number of non-patient genome sequences to be included.

To that end, the inventors contemplate methods of identifying the presence of a non-patient nucleic acid in a diseased tissue of a patient in which a reference sequence for genome analysis is modified by informationally coupling an editing engine to a sequence database that stores one or more nucleic acid sequences from mammalian tissues and one or more non-patient nucleic acid sequences from respective distinct sources (e.g., different viruses, different pathogens, different bacteria, combinations thereof, etc). The editing engine is then used to merge the nucleic acid sequence(s) from the mammalian tissue with the plurality of non-patient nucleic acid sequences into a single chimeric nucleic acid sequence file. Of course, it should be appreciated that such editing can be performed manually using a relatively small number of selected non-patient genomic sequences, or in an automated fashion where the collection of viruses is relatively large. Moreover, it should be appreciated that the editing engine may merge the non-patient sequences in any format to the (e.g., mammalian/human) reference sequence, and that the non-patient sequences may be transformed in the desired end format (e.g., BAM, SAM, FASTA, or FASTA index format) at any given time. However, it is generally preferred that the non-patient sequences are already in the desired end format (e.g., BAM, SAM, FASTA, or FASTA index format). For example, the reference sequence or reference sequences may be stored in a FASTA file with an associated FASTA Index, and that file may then be merged with one or more non-patient genome sequences as noted above. Further conversion in BAM format can be performed if desired/needed. Furthermore, the sequencing data from the patient's diseased issue that contain non-patient sequences may also be stored in the BAM file.

Moreover, with respect to the structure of the chimeric nucleic acid sequence, it is especially preferred that the nucleic acid sequence from the mammalian tissue is organized in the single chimeric nucleic acid sequence file following a chromosomal structure (as is, for example, the case in a BAM format), while the viral nucleic acid sequences are organized in the single chimeric nucleic acid sequence file as respective single chromosomes. Once the chimeric nucleic acid sequence file has been assembled, it is preferred that the sequence database is then updated with the so produced chimeric nucleic acid sequence file. Of course, it should also be recognized that the editing engine may also be employed for on-the-fly merging of the nucleic acid sequence from a mammalian tissue with one or more viral nucleic acid sequences from a library of virus genome sequences such that incremental synchronous alignment can be performed as further discussed below. With respect to suitable sequences and portions thereof, the same considerations as already provided above apply.

In further particularly preferred aspects of the inventive subject matter, the chimeric reference nucleic acid sequence and the nucleic acid sequence from the virus-associated tumor are processed using incremental synchronized alignment to enable rapid identification of integration, co-amplification, and location of genomic exchange. For example, and while not limiting the inventive subject matter, it is generally preferred that the genomic analysis is performed using a software tool in which a chimeric reference nucleic acid sequence (that includes genomic nucleic acid sequence from healthy or reference tissue) is synchronized and incrementally compared against the nucleic acid sequence from the virus-associated tumor (or other diseased tissue). One especially preferred tool includes BAMBAM as previously described in WO2013/074058A1, incorporated herein by reference in its entirety.

Using such approach, it should be especially appreciated that not only presence of cross-species integrated sequences can be found in the respective samples (e.g., virus and patient), but also the location, copy number, mutations, etc, all of which may have significant impact in terms of disease presence, progression, and/or outcome. In particular, where integration of viral sequences in patient genome is associated with an increase in genomic mutations, mutations in the viral sequence integrated into the patient genome may be detected as well. Thus, the inventors not only contemplate a method of detecting one or more cross-species integration events, but also a characterization of such events that is then used as a basis for evaluation of treatment and prognosis.

For example, the inventors further contemplate a method in which an analysis engine is informationally coupled to a sequence database storing a nucleic acid sequence from a cervical tumor of a patient and a chimeric reference nucleic acid sequence, wherein the chimeric reference nucleic acid sequence comprises a reference sequence (preferably a matched normal nucleic acid sequence) from the patient and one or more viral nucleic acid sequences of an HPV virus. An analysis engine is then used to identify an integration of at least some of the viral nucleic acid sequence in the chimeric reference nucleic acid sequence with at least one allele of an oncogene (e.g., gene encoding a growth factor receptor, including ERBB2, or a tumor suppressor gene, a gene involved in cell cycle regulation, and/or a gene involved in division of a cell) in the nucleic acid sequence from the cervical tumor.

It is generally preferred that the reference sequence is used to calculate a plurality of epitopes. Most typically, the epitopes will be calculated to have a length of between 2-50 amino acids, more typically between 5-30 amino acids, and most typically between 9-15 amino acids. Such epitopes may incrementally cover the entire reference sequence, or may only cover specific portions (e.g., exons only). Likewise, the non-patient nucleic acid is then employed to calculate a plurality of neoepitopes, at least for positions in which the non-patient nucleic acid differs from the reference sequence. The so calculated epitopes and neoepitopes are then analyzed in silico for their affinity to the patient-specific HLA-type as further described below in more detail.

It should be appreciated that knowledge of HLA affinity for such neoepitopes provides at least two items of valuable information: (a) deletion of an epitope otherwise suitable for immunotherapy can be recognized and immunotherapy be adjusted accordingly so as to not target the deleted epitope, and (b) generation of a neoepitope suitable for immunotherapy can be recognized and immunotherapy be adjusted accordingly so as to target the neoepitope. It should further be recognized that such change in epitopes is particularly relevant for diseases in which the nucleic acid for the pathogen (or oncogene or tumor suppressor gene) is subject to increased rates of mutations. Such increased rate of mutations may be due to genomic instability, which may be introduced by pathogen or other genetic defects (e.g., via interference of viral E6/E7 gene product), exposure to chemotherapeutic drugs or radiation, etc. Viewed from a different perspective, immunotherapeutic treatment options can be adjusted or predicted and so may lead to more effective treatment.

With respect to neoepitope it should be appreciated that neoepitopes can be characterized as random mutations in tumor cells that create unique and tumor specific antigens. Therefore, high-throughput genome sequencing should allow for rapid and specific identification of patient specific neoepitopes where the analysis also considers matched normal tissue of the same patient. Notably, as also disclosed in our U.S. provisional application 62/144,745 incorporated herein by reference in its entirety, very few neoepitopes appear to be required to illicit an immune response and consequently present a unique opportunity for the manufacture of cancer immunotherapies.

In especially preferred aspects, tumor-specific neoepitopes are identified using at least two criteria: First, a mutation in a tumor genomic sample is identified against a matched normal sample of a patient to detect presence of a non-patient (or previously mutated patient) nucleic acid in the omics data, and second, the non-patient (or previously mutated patient) nucleic acid is then correlated with a reference nucleic acid of a pathogen or prior mutated nucleic acid sequence of the same patient. Of course, it should be noted that sequences with a confirmed expression are generally preferred for subsequent analysis.

Of course, it should also be appreciated that further downstream analysis may be performed on identified sequence differences to identify those that lead to a new peptide sequence based on the cancer and patient specific mutation. In other words, silent mutations may be eliminated from the list of identified neoepitopes. Neoepitopes may therefore be identified by considering the type (e.g., deletion, insertion, transversion, transition, translocation) and impact of the mutation (e.g., non-sense, missense, frame shift, etc.), and may as such serve as a first content filter through which silent and other non-relevant (e.g., non-expressed) mutations are eliminated. It should further be appreciated that neoepitope sequences can be defined as sequence stretches with relatively short length (e.g., 7-11 mers) wherein such stretches will include the change(s) in the amino acid sequences. Most typically, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is an amino acid and N is a changed amino acid (relative to wild type or matched normal).

It should further be appreciated that neoepitope sequences as contemplated herein can be defined as sequence stretches with relatively short length (e.g., 5-30 mers, more typically 7-11 mers, or 12-25 mers) wherein such stretches include the change(s) in the amino acid sequences. Most typically, the change(s) is/are located centrally or near the center (e.g., less than 4, or less than 5, or less than 6 amino acids from center position). Therefore, and viewed from a different perspective, neoepitope sequences contemplated herein will especially include those in which a single amino acid is exchanged relative to the matched normal sequence, and in which the position of the changed amino acid is centrally located, or near the center of the neoepitope sequence (e.g., in a 9-mer, the changed amino acid is at position 2, 3, 4, or 5, and more typically at position 3, 4, or 5, and most typically at position 4 or 5). Thus, it should be appreciated that a single amino acid change may be presented in numerous neoepitope sequences that include the changed amino acid, depending on the position of the changed amino acid. Advantageously, such sequence variability allows for multiple choices of neoepitopes and so increases the number of potentially useful targets that can then be selected on the basis of one or more desirable traits (e.g., highest affinity to a patient HLA-type, highest structural stability, etc.). Most typically, neoepitopes will be calculated to have a length of between 2-50 amino acids, more typically between 5-30 amino acids, and most typically between 9-15 amino acids, with a changed amino acid preferably centrally located or otherwise situated in a manner that improves its binding to major histocompatibility complex (MHC).

For example, where the epitope is to be presented by the MHC-I complex, a typical epitope length will be about 8-11 amino acids, while the typical epitope length for presentation via MHC-II complex will have a length of about 13-17 amino acids. As will be readily appreciated, since the position of the changed amino acid in the neoepitope may be other than central, the actual peptide sequence and with that actual topology of the neoepitope may vary considerably. Moreover, where the neoepitope is presented to an immune competent (or other) cell as a synthetic peptide, it should be appreciated that the synthetic peptide may be significantly longer than the peptide portion that is ultimately bound by the MHC-I or MHC-II system to so allow for proteolytic processing in the cell. For example, contemplated synthetic peptides may therefore have between 8 and 15 amino acids upstream and downstream of the changed amino acid.

In preferred embodiments facilitating computational analysis (and as noted above), it is contemplated that analysis of epitopes and neoepitopes will be confined to relatively small fragments having a minimum size necessary for antibody binding (e.g., at least 5-6 amino acids) and a maximum size of 20 amino acids (and in some cases longer). Therefore, epitopes and neoepitopes will preferably have a length of between 7-12 amino acids. For example, suitable neoepitopes may have a length of nine amino acids, including the changed amino acid.

It is generally contemplated that genomic analysis can be performed by any number of analytic methods, however, especially preferred analytic methods include WGS (whole genome sequencing) and exome sequencing of both tumor and matched normal sample. Likewise, the computational analysis of the sequence data may be performed in numerous manners. In most preferred methods, however, analysis is performed in silico by location-guided synchronous alignment of tumor and normal samples as, for example, disclosed in US 2012/0059670A1 and US 2012/0066001A1, each incorporated herein by reference in its entirety, using BAM files and BAM servers. It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

Consequently, it should be recognized that patient and cancer specific neoepitopes can be identified in an exclusively in silico environment that ultimately predicts potential epitopes or neoepitopes that are unique to the patient and tumor type. So identified and selected epitopes or neoepitopes can then be further filtered in silico against an identified patient HLA-type. Such HLA-matching is thought to ensure strong binding of the epitopes or neoepitopes to the MHC complex and so assist in triggering an immune response to the epitope or neoepitope. It should be further appreciated that the selected or identified neoepitopes can be non-native to the patient. However, it should be appreciated that alternative or additional filtering methods can be used to identify epitopes and neoepitopes of interest.

With respect to filtering identified neoepitopes, it is generally contemplated that neoepitopes are especially suitable for use herein where omics (or other) analysis reveals that the neoepitope is actually expressed. Identification of expression and expression level of a neoepitope can be performed in all manners known in the art and preferred methods include RNA-seq, quantitative RNA (hnRNA or mRNA) analysis and/or quantitative proteomics analysis. Most typically, the threshold level for inclusion of neoepitopes will be an expression level of at least 20%, and more typically at least 50% of expression level of the corresponding matched normal sequence, thus ensuring that the (neo)epitope is at least potentially 'visible' to the immune system. Consequently, it is generally preferred that the omics analysis also includes an analysis of gene expression (transcriptomic analysis) to so help identify the level of expression for the gene with a mutation. There are numerous methods of transcriptomic analysis know in the art, and all of the known methods are deemed suitable for use herein. For example, preferred materials include mRNA and primary transcripts (hnRNA), and RNA sequence information may be obtained from reverse transcribed polyA$^+$-RNA, which is in turn obtained from a tumor sample and a matched normal (healthy) sample of the same patient. Likewise, it should be noted that while polyA$^+$-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis. Most typically, RNA quantification and sequencing is performed using qPCR and/or rtPCR based methods, although other methods (e.g., solid phase hybridization-based methods) are also deemed suitable. Viewed from another perspective, transcriptomic analysis may be suitable (alone or in combination with genomic analysis) to identify and quantify genes having a cancer and patient specific mutation.

Taking the above into consideration, it should therefore be appreciated that a patient sample comprising DNA and RNA from tumor and matched normal tissue can be used to identify specific mutations and to quantify such mutations.

Similarly, proteomics analysis can be performed in numerous manners to ascertain expression of the neoepitope, and all known manners or proteomics analysis are contemplated herein. However, particularly preferred proteomics methods include antibody-based methods and mass spectroscopic methods (e.g., SRM, CRM, MRM). Moreover, it should be noted that the proteomics analysis may not only provide qualitative or quantitative information about the protein per se, but may also include protein activity data where the protein has catalytic or other functional activity. One example of a technique for conducting proteomic assays includes U.S. Pat. No. 7,473,532 to Darfler et al. titled "Liquid Tissue Preparation from Histopathologically Processed Biological Samples, Tissues, and Cells" filed on Mar. 10, 2004, incorporated herein by reference in its entirety.

In addition, neoepitopes may also be subject to detailed analysis and filtering using predefined structural and/or sub-cellular location parameters. For example, it is contemplated that neoepitope sequences are selected for further use if they are identified as having a membrane associated location (e.g., are located at the outside of a cell membrane of a cell) and/or if in silico structural calculation confirms that the neoepitope is likely to be solvent exposed or presents a structurally stable epitope, etc.

In yet another aspect of filtering, the neoepitopes may be compared against a database that contains known human sequences to so avoid use of a human-identical sequence. Moreover, filtering may also include removal of neoepitope sequences that are due to SNPs in the patient. For example, The Single Nucleotide Polymorphism Database (dbSNP) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (i.e., single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation. Using such database, the patient and tumor specific neoepitopes may be further filtered to remove those know sequences, yielding a therapeutic sequence set with a plurality of neoepitope sequences.

In some embodiments neoepitopes can be scored/ranked based on allele frequency multiplied by the transcripts per million number to get a likelihood score. This score can then be further augmented using HLA information and calculated or actual binding affinity to the patient's HLA type. For example, an exemplary ranking format may be:
>254 NM_001000.3 RPL39 Missense p.M29K A→T Normal: WI RMKTGNK, AF: 0.179104477612 TPM: 1023.96 TPM_MEDIAN: 7.35 LL: 183.395820896 netM HC: 242.96 Allele: HLA-A0301 WIRKKTGNK.

Here, the file is a FASTA formatted file, and entries start with the '>' character, which just reports sample information. The next line is the neoepitope. In the sample information line contains a number used for indexing the sample (e.g., 254), the Refseq Gene ID (e.g., NM_001000.3), the HUGO common name (e.g., RPL39), the variant classification (e.g., Missense), the protein change (e.g., p.M29K), the base pair change (e.g., A→T), the normal epitope (e.g., Normal: WIRMKTGNK (SEQ. ID No. 24), allele frequency (e.g., AF: 0.179104477612), Transcripts per million for this gene (e.g., TPM: 1023.96), TPM_MEDIAN which is the median expression level of all the genes (e.g., TPM_MEDIAN: 7.35), the LL score which is just AF×TPM (e.g., LL: 183.395820896), the netMHC predicted binding value (e.g., netMHC: 242.96), and the specific HLA allele that the neoepitope binds to (e.g., Allele: HLA-A0301). The next line is then the neoepitope (e.g., WIRKKTGNK (SEQ. ID No. 25)).

It should be recognized that synchronized incremental analysis and enormous size of sequence files will render methods of the inventive subject matter entirely unsuitable for human practice as such file analysis would readily exceed the lifespan of a human, even if one would analyze 10,000s of bases per day. Moreover, calculation of solutions for genomic arrangements will further add to the impossibility of human action. In addition, it should be pointed out that the particular file structure of the chimeric reference nucleic acid (i.e., merged viral nucleic acid sequence and mammalian nucleic acid sequence, with viral sequences organized/indexed as individual chromosomes) will have the technical effect of drastically improving analysis time as such file structure (a) can be rapidly processed without much memory demand as compared to loading an entire sequence into memory, and (b) allows for rapid analysis of genomic integration and identification of epitopes or neoepitopes as such method requires only analysis of two sequence files rather than three or more as otherwise dictated by the number of sources for non-patient omics.

HLA determination can be performed using various methods in wet-chemistry that are well known in the art, and all of these methods are deemed suitable for use herein. However, in especially preferred methods, the HLA-type can also be predicted from omics data in silico using a reference sequence containing most or all of the known and/or common HLA-types as is shown in more detail below. In short, a patient's HLA-type is ascertained (using wet chemistry or in silico determination), and a structural solution for the HLA-type is calculated or obtained from a database, which is then used as a docking model in silico to determine binding affinity of the neoepitope to the HLA structural solution. Suitable systems for determination of binding affinities include the NetMHC platform (see e.g., Nucleic Acids Res. 2008 Jul. 1; 36 (Web Server issue): W509-W512). Neoepitopes with high affinity (e.g., less than 100 nM, less than 75 nM, less than 50 nM) against the previously determined HLA-type are then selected. In calculating the highest affinity, modifications to the neoepitopes may be implemented by adding N- and/or C-terminal modifications to the epitope to further increase binding of the virally expressed neoepitope to the HLA-type. Thus, neoepitopes may be native as identified or further modified to better match a particular HLA-type.

In some aspects, HLA typing involves a method of in silico predicting an HLA-type for a patient in which a reference sequence is provided that includes a plurality of sequences of known and distinct HLA alleles, and in which a plurality of patient sequence reads are provided, wherein at least some of the patient sequence reads include a sequence encoding a patient specific HLA. In a further step, the patient sequence reads are decomposed into a plurality of respective sets of k-mers, and a composite de Bruijn graph is then generated using the reference sequence and the plurality of respective sets of k-mers. It is further contemplated that each of the known and distinct HLA alleles are ranked using a composite match score that is calculated from respective votes of the plurality of patient sequence reads, wherein each vote uses k-mers that match corresponding segments in the known and distinct HLA alleles.

In preferred embodiments, omics data may be analyzed using a colored De Bruijn graph where the edges are k-mers (k=15) having "colors" that identify which input source the k-mer is found in (e.g., reference, normal sample, and/or tumor sample, samples taken at different times or ages, samples from different patient or subject groups, etc.), and where each edge is connected to adjacent edges. Exemplary systems and methods are described in U.S. provisional application 62/209,858. For example, a first graph can be constructed from a reference sequence to store k-mer positions in a genome. It should be noted that this reference sequence is built from all known (or at least all common HLA-type sequences). Preferably, and depending on the particular task required, the k-mers will have a length of between 3 and 300 bases, more preferably between 10-100 bases, and most preferably between 10-20 or 13-18 bases (e.g., k=13). Once the first graph is established, k-mers from tumor and normal raw sequencing data located in a given region of genome (including unmapped anchored reads) are added. As needed, weak edges can be pruned from the graph to remove reads for which maximal support is below a specific user defined threshold (e.g., where k=13, threshold is 8). Such pruning will typically increase accuracy of the sequence prediction/alignment.

In a further step, the so constructed composite graph is analyzed for junctions at which tumor and reference diverge. For each divergence, a depth-first search is employed to identify all unique paths through tumor edges that result in tumor converging with reference, which can be expressed as a bubble (points of divergence and convergence driven by the differences in sequence information using the k-mers).

Statistical analysis from the end of each bubble solution can then be employed to identify the most likely alignment and/or sequence. As in most typical embodiments the sequences are not mere raw sequence reads but annotated SAM or BAM files, statistical analysis can include read specific parameters based on the metadata for each read. Therefore, statistical analysis may include maximal support, mapping/base qualities for k-mers, support in the matched-normal, etc. As a result, it should be recognized that back-tracking along reference edges to reconstruct the reference sequence and determination of location in the genome can be performed for paths in the graph that meet typically user defined criteria (e.g., min support>X reads, max support in normal<Y reads, etc.). So reconstructed sequences and/or structures can then be used to classify the specific variant. Preferably, the variant classification is presented in a VCF format, although other formats are also contemplated.

As noted before, HLA/MHC reference sequences typically comprise a library of known alleles that is then used to form a reference graph that is then used to build a composite graph using patient DNA or RNA. For example, for HLA prediction for a patient sample, a graph from all alleles for a given HLA type (A, B, C, G, DRB1, . . . ) is constructed. While not limiting to the inventive subject matter, paired sequencing reads from a single patient BAM file are joined as fragments and "threaded" through the HLA-A graph and ranked to thereby establish a best fit. For example, HLA alleles that have the best (or equivalent) similarity to the fragment in question (defined as fraction of shared k-mers) increment their score by 1 count for each shared k-mer, and top HLA alleles may then be chosen according to their scores. Of course, it should be noted that other metrics may also be collected (e.g., overall coverage depth, graph edges, fraction of HLA sequence covered by fragments, etc.) and used for scoring.

Most typically, the HLA-reference sequence includes alleles for at least one HLA type that have an allele frequency of at least 1%, or the reference sequence includes at least ten different alleles for at least one HLA type, and/or alleles for at least two distinct HLA types. With respect to the HLA type it is contemplated that suitable HLA-types include an HLA-A type, an HLA-B type, an HLA-C type, a HLA-DRB-1 type, and/or a HLA-DQB-1 type.

In one exemplary aspect of the inventive subject matter, a relatively large number of patient sequence reads mapping to chromosome 6p21.3 (or any other location near/at which HLA alleles are found) is provided by a database or sequencing machine. Most typically the sequence reads will have a length of about 100-300 bases and comprise metadata, including read quality, alignment information, orientation, location, etc. For example, suitable formats include SAM, BAM, FASTA, GAR, etc. While not limiting to the inventive subject matter, it is generally preferred that the patient sequence reads provide a depth of coverage of at least 5×, more typically at least 10×, even more typically at least 20×, and most typically at least 30×.

In addition to the patient sequence reads, contemplated methods further employ one or more reference sequences that include a plurality of sequences of known and distinct HLA alleles. For example, a typical reference sequence may be a synthetic (without corresponding human or other mammalian counterpart) sequence that includes sequence segments of at least one HLA-type with multiple HLA-alleles of that HLA-type. For example, suitable reference sequences include a collection of known genomic sequences for at least 50 different alleles of HLA-A. Alternatively, or additionally, the reference sequence may also include a collection of known RNA sequences for at least 50 different alleles of HLA-A. Of course, and as further discussed in more detail below, the reference sequence is not limited to 50 alleles of HLA-A, but may have alternative composition with respect to HLA-type and number/composition of alleles. Most typically, the reference sequence will be in a computer readable format and will be provided from a database or other data storage device. For example, suitable reference sequence formats include FASTA, FASTQ, EMBL, GCG, or GenBank format, and may be directly obtained or built from data of a public data repository (e.g., IMGT, the International ImMunoGeneTics information system, or The Allele Frequency Net Database, EUROSTAM, www.allelefrequencies.net). Alternatively, the reference sequence may also be built from individual known HLA-alleles based on one or more pre-determined criteria such as allele frequency, ethnic allele distribution, common or rare allele types, etc.

Using the reference sequence, the patient sequence reads can now be threaded through a de Bruijn graph to identify the alleles with the best fit. In this context, it should be noted that each individual carries two alleles for each HLA-type, and that these alleles may be very similar, or in some cases even identical. Such high degree of similarity poses a significant problem for traditional alignment schemes. It is contemplated that HLA alleles, and even very closely related alleles can be resolved using an approach in which the de Bruijn graph is constructed by decomposing a sequence read into relatively small k-mers (typically having a length of between 10-20 bases), and by implementing a weighted vote process in which each patient sequence read provides a vote ("quantitative read support") for each of the alleles on the basis of k-mers of that sequence read that match the sequence of the allele. The cumulatively highest vote for an allele then indicates the most likely predicted HLA allele. In addition, it is generally preferred that each fragment that is a match to the allele is also used to calculate the overall coverage and depth of coverage for that allele. Further aspects, suitable methods and considerations for high-accuracy in silico HLA typing are described in commonly owned International PCT/US16/48768, incorporated herein by reference in its entirety.

Scoring may further be improved or refined as needed, especially where many of the top hits are similar (e.g., where a significant portion of their score comes from a highly shared set of k-mers). For example, score refinement may include a weighting scheme in which alleles that are substantially similar (e.g., >99%, or other predetermined value) to the current top hit are removed from future consideration. Counts for k-mers used by the current top hit are then re-weighted by a factor (e.g., 0.5), and the scores for each HLA allele are recalculated by summing these weighted counts. This selection process is repeated to find a new top hit. The accuracy of the method can be even further improved using RNA sequence data that allows identification of the alleles expressed by a tumor, which may sometimes be just 1 of the 2 alleles present in the DNA. In further advantageous aspects of contemplated systems and methods, DNA or RNA, or a combination of both DNA and RNA can be processed to make HLA predictions that are highly accurate and can be derived from tumor or blood DNA or RNA.

Such refining is particularly advantageous for HLA determination from DNA and/or RNA sequencing information since each HLA-type has numerous often very similar alleles, and as traditional alignment methods typically fail to have significant differentiation capabilities where sequences have high degree of similarity.

Of course, it should be appreciated that the analysis and HLA prediction need not be limited to the particular HLA-types shown above, but that all HLA-types and allelic variants are contemplated herein, including HLA-E, HLA-F, HLA-G, HLA-H, HLA-J, HLA-K, HLA-L, HLA-V, HLA-DQA1, HLA-DMA, HLA-DMB, HLA-DOA, HLA-DOB, HLA-DPA1, HLA-DPB1, HLA-DRA, HLA-DRB345, HLA-MICA, HLA-MICB, HLA-TAP1, HLA-TAP2, and even newly discovered HLA types and their corresponding alleles. Moreover, it should be appreciated that the analysis need not be limited to a single HLA-type, but that multiple HLA-types are suitable for use herein. Consequently, the reference sequence may include two, three, four, or more HLA-types, with a collection of alleles for the respective HLA-types. As each HLA-type has a significant number of alleles, it is contemplated that not all of the known alleles need to be included in the reference sequence. For example, the reference sequence may include alleles with an allele frequency above a particular threshold such as an allele frequency of at least 0.1%, or at least 0.5%, or at least 1%, or at least 2%, or at least 5%. Therefore, and viewed from a different perspective, suitable reference sequences may include at least 10, or at least 30, or at least 50, or at least 100, or at least 200 or at least 500, or even more different alleles for at least one HLA type.

Once patient and tumor specific neoepitopes and HLA-type are identified, computational analysis can be performed by docking neoepitopes to the HLA and determining best binders (e.g., lowest $K_D$, for example, less than 50 nM). It should be appreciated that such approach will not only identify specific neoepitopes that are genuine to the patient and tumor, but also those neoepitopes that are most likely to be presented on a cell and as such most likely to elicit an immune response with therapeutic effect. Of course, it should also be appreciated that thusly identified HLA-matched neoepitopes can be biochemically validated in vitro prior to inclusion of the nucleic acid encoding the epitope as payload into the virus as further discussed below.

Of course, it should be appreciated that matching of the patient's HLA-type to the patient- and cancer-specific neoepitope can be done using systems other than NetMHC, and suitable systems include NetMHC II, NetMHCpan, IEDB Analysis Resource (URL immuneepitope.org), Rank-Pep, PREDEP, SVMHC, Epipredict, HLABinding, and others (see e.g., J Immunol Methods 2011; 374:1-4). In calculating the highest affinity, it should be noted that the collection of neoepitope sequences in which the position of the altered amino acid is moved (supra) can be used. Alternatively, or additionally, modifications to the neoepitopes may be implemented by adding N- and/or C-terminal modifications to further increase binding of the expressed neoepitope to the patient's HLA-type. Thus, neoepitopes may be native as identified or further modified to better match a particular HLA-type.

Moreover, where desired, binding of corresponding wild-type sequences (i.e., neoepitope sequence without amino acid change) can be calculated to ensure high differential affinities. For example, especially preferred high differential affinities in MHC binding between the neoepitope and its corresponding wildtype sequence are at least 2-fold, at least 5-fold, at least 10-fold, at least 100-fold, at least 500-fold, at least 1000-fold, etc.).

It should be appreciated that such methods provide the advantage of identifying new viral epitopes for immunotherapy treatment based on specific mutations in a specific patient genome, including specific mutations of viral sequences integrated into the specific patient genome. Such viral epitopes cannot be identified by "traditional" vaccination protocols.

With respect to the 'payload' of the genetically modified adenovirus it is contemplated that expression of more than one neoepitope is preferred, for example two, three, four, five, and even more, which can be accomplished using multiple distinct modified viruses, or a virus having more than one neoepitope sequence (e.g., as concatemeric or chimeric sequence).

Identified HLA-matched neoepitopes will then be preferably used in one or more types of patient-, tumor-, and location-specific immunotherapy. For example, immunotherapy may include virally mediated cancer antigen delivery for expression to elicit an immune response, which may be further augmented with checkpoint inhibitors. On the other hand, patient-, tumor-, and location-specific antibodies (or synthetic antibodies) against so identified neoepitopes may be employed as targeting moieties for drugs or radiochemicals, or used in conjunction with NK cells to elicit a cytotoxic T-cell response.

Where recombinant viruses are employed, it is contemplated that all known manners of making recombinant viruses are deemed suitable for use herein, however, especially preferred viruses are those already established in gene therapy, including adenoviruses, adeno-associated viruses, alphaviruses, herpes viruses, lentiviruses, etc. However, among other appropriate choices, adenoviruses are particularly preferred. Moreover, it is further generally preferred that the virus is a replication deficient and non-immunogenic virus, which is typically accomplished by targeted deletion of selected viral proteins (e.g., E1, E3 proteins). Such desirable properties may be further enhanced by deleting E2b gene function, and high titers of recombinant viruses can be achieved using genetically modified human 293 cells as has been recently reported (e.g., J Virol. 1998 February; 72(2): 926-933). Most typically, the desired nucleic acid sequences (for expression from virus infected cells) are under the control of appropriate regulatory elements well known in the art.

Most preferably, therapeutic preparations of recombinant nucleic acid(s) encode cancer associated or cancer-specific epitopes, or patient-specific neoepitopes in an arrangement such that the epitopes are directed to MHC-I and/or MHC-II presentation pathways. Such immune stimulation is thought to produce a more robust immune response, which is further augmented by subcutaneous delivery or (more typically) expression of co-stimulatory molecules and/or checkpoint inhibitors. Of course, it should be appreciated that all manners of delivery of such recombinant nucleic acid(s) are deemed suitable and that the recombinant nucleic acid(s) may be formulated as a DNA vaccine, be part of a recombinant viral genome, or deliverable in a transfection composition. Moreover, subcutaneous administration of the viral vehicle (and optional checkpoint inhibitors such as pembrolizumab, nivolumab, ipilimumab) will lead to an appropriate B-cell response and concomitant IgG1 production, which can be amplified using transfused NK cells. Most preferably, modified NK cells will include high affinity Fcγ receptors (CD16) and may further express chimeric antigen receptors (with high specificity toward tumor associated epitopes and/or neoepitopes).

Viruses may be used individually or in combination as a therapeutic vaccine in a pharmaceutical composition, typically formulated as a sterile injectable composition with a virus titer of between $10^4$-$10^{11}$ virus particles per dosage unit. However, alternative formulations are also deemed suitable for use herein, and all known routes and modes of administration are contemplated herein. As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.).

In most preferred aspects, signal peptides may be used for trafficking to the endosomal and lysosomal compartment, or for retention in the cytoplasmic space. For example, where the peptide is to be exported to the endosomal and lysosomal compartment targeting presequences and the internal targeting peptides can be employed. The presequences of the targeting peptide are preferably added to the N-terminus and comprise between 6-136 basic and hydrophobic amino acids. In case of peroxisomal targeting, the targeting sequence may be at the C-terminus. Other signals (e.g., signal patches) may be used and include sequence elements that are separate in the peptide sequence and become functional upon proper peptide folding. In addition, protein modifications like glycosylations can induce targeting. Among other suitable targeting signals, the inventors contemplate peroxisome targeting signal 1 (PTS1), a C-terminal tripeptide, and peroxisome targeting signal 2 (PTS2), which is a nonapeptide located near the N-terminus. In addition, sorting of proteins to endosomes and lysosomes may also be mediated by signals within the cytosolic domains of the proteins, typically comprising short, linear sequences. Some signals are referred to as tyrosine-based sorting signals and conform to the NPXY or YXXØ consensus motifs. Other signals known as dileucine-based signals fit [DE]XXXL[LI] or DXXLL consensus motifs. All of these signals are recognized by components of protein coats peripherally associated with the cytosolic face of membranes. YXXØ and [DE]XXXL[LI] signals are recognized with characteristic fine specificity by the adaptor protein (AP) complexes AP-1, AP-2, AP-3, and AP-4, whereas DXXLL signals are recognized by another family of adaptors known as GGAs. Also FYVE domain can be added, which has been associated with vacuolar protein sorting and endosome function. In still further aspects, endosomal compartments can also be targeted using human CD1 tail sequences (see e.g., *Immunology*, 122, 522-531).

It should be appreciated that such methods allow for specific delivery of a peptide to an MHC subtype having the highest affinity with the peptide, even if that peptide would otherwise not be presented by that MHC subtype.

Trafficking to or retention in the cytosolic compartment may not necessarily require one or more specific sequence elements. However, in at least some aspects, N- or C-terminal cytoplasmic retention signals may be added, including a membrane-anchored protein or a membrane anchor domain of a membrane-anchored protein. For example, membrane-anchored proteins include SNAP-25, syntaxin, synaptoprevin, synaptotagmin, vesicle associated membrane proteins (VAMPs), synaptic vesicle glycoproteins (SV2), high affinity choline transporters, Neurexins, voltage-gated calcium channels, acetylcholinesterase, and NOTCH.

In yet further contemplated aspects, it should be noted that the various neoepitopes may be arranged in numerous manners, and that a transcription or translation unit may have concatemeric arrangement of multiple epitopes, typically separated by short linkers (e.g., flexible linkers having between 4 and 20 amino acids), which may further include protease cleavage sites. Such concatemers may have between 1 and 20 neoepitopes (typically limited by size of recombinant nucleic acid that can be delivered via a virus), and it should be noted that the concatemers may be identical for delivery to the MHC-I and MHC-II complex, or different. Therefore, it should be appreciated that various peptides can be routed to specific cellular compartments to so achieve preferential or even specific presentation via MHC-I and/or MHC-II. Viewed from another perspective, it should be recognized that tumor associated antigens and neoepitopes may be presented via both presentation pathways, or selectively to one or another pathway at the same time or in subsequent rounds of treatment. With respect to further suitable configurations and expression cassettes reference is made to U.S. provisional application 62/302,168 with the title "Compositions And Methods For Coordinated Antigen Presentation", filed on or about Feb. 11, 2016 and incorporated herein by reference in its entirety.

While not limiting to the inventive subject matter, it is generally preferred that neoepitope sequences are configured as a tandem minigene (e.g., $aa_{12}$-$neoepitope_{12}$-$aa_{12}$), or as single transcriptional unit, which may or may not be translated to a chimeric protein. Thus, it should be appreciated that the epitopes can be presented as monomers, multimers, individually or concatemeric, or as hybrid sequences with N- and/or C-terminal peptides as already discussed above. Most typically, it is preferred that the nucleic acid sequence is back-translated using suitable codon usage to accommodate the virus and/or host codon preference. However, alternate codon usage or non-matched codon usage is also deemed appropriate.

Additionally, it is preferred that the viral delivery vehicle also encodes at least one, more typically at least two, even more typically at least three, and most typically at least four co-stimulatory molecules to enhance the interaction between the infected dendritic cells and T-cells. For example, suitable co-stimulatory molecules include ICAM-1 (CD54), ICOS-L, and LFA-3 (CD58), especially in combination with B7.1 (CD80) and/or B7.2 (CD86). Further contemplated co-stimulatory molecules include 4-1BBL, CD30L, CD40, CD40L, CD48, CD70, CD112, CD155, GITRL, OX40L, and TL1A. Moreover, it should be appreciated that expression of the co-stimulatory molecules will preferably be coordinated such that the antigens and/or neoepitopes are presented along with one or more co-stimulatory molecules. Thus, it is typically contemplated that the co-stimulatory molecules are produced from a single transcript using an internal ribosome entry site or 2A sequence, or from multiple transcripts.

Likewise, it is contemplated that the viral vector will further include a sequence portion that encodes one or more peptide ligands that bind to a checkpoint receptor. Most typically, binding will inhibit or at least reduce signaling via the receptor, and particularly contemplated receptors include CTLA-4 (especially for CD8+ cells) PD-1 (especially for CD4+ cells). For example, peptide binders can include antibody fragments and especially scFv, but also small molecule peptide ligands that specifically bind to the receptors. Once more, it should be appreciated that expression of the peptide molecules will preferably be coordinated such that the antigens and/or neoepitopes are presented along with one or more peptide molecules. Thus, it is typically contemplated that the peptide molecules are produced from a single transcript using an internal ribosome entry site or 2A sequence, or from multiple transcripts.

Lastly, it should be noted that where the virus comprises a nucleic acid payload that encodes multiple neoepitopes, it is contemplated that multiple neoepitopes may at least additively or synergistically enhance the host immune response. Similarly, where multiple viruses are used with each virus having a different neoepitope, it is contemplated that multiple neoepitopes may at least additively or synergistically enhance the host immune response. Such additive or synergistic effect may be genuine to a specific tumor or stage, or specific to particular patient parameter (e.g., age, gender, previous treatment, etc.)

Synthetic antibodies against one or more patient and virus specific neoepitopes can be generated by in silico analysis of omics data (typically whole genome sequencing and expression profiling) to obtain unique neoepitope sequences having a n-mer length (typically 7-11 mers). These sequences are then used to prepare actual peptide sequences. For example, peptides with cancer neoepitope sequences can be prepared on a solid phase (e.g., using Merrified synthesis), via liquid phase synthesis, or from smaller peptide fragments. In less preferred aspects, peptides could also be produced by expression of a recombinant nucleic acid in a suitable host (especially where multiple neoepitopes are on a single peptide chain, optionally with spacers between neoepitopes or cleavage sites). The peptides are immobilized to a solid phase and used as bait for fishing antibodies with specific binding affinity to the neoepitopes. Antibodies are then analyzed, and synthetic recombinant antibodies are prepared using the results of the analysis. Thusly produced synthetic antibodies ('synbodies') are consequently expected to bind with high specificity to the patient specific epitopes. Most notably, such synbodies are generated entirely artificially using only information gleaned from computational analysis of a patients mutations.

For example, one or more of the peptide neoepitopes (e.g., 9-mers) can be immobilized on a solid carrier (e.g., magnetic or color coded bead) and used as a bait to bind surface presented antibody fragments or antibodies. Most typically, such surface presented antibody fragments or antibodies are associated with a M13 phage (e.g., protein III, VIII, etc.) and numerous libraries for antibody fragments are known in the art and suitable in conjunction with the teachings presented herein. Where desired, smaller libraries may also be used and be subjected to affinity maturation to improve binding affinity and/or kinetic using methods well known in the art (see e.g., Briefings in functional genomics and proteomics. Vol 1. No 2. 189-203. July 2002). In addition, it should be noted that while antibody libraries are generally preferred, other scaffolds are also deemed suitable and include beta barrels, ribosome display, cell surface display, etc. (see e.g., Protein Sci. 2006 January; 15(1): 14-27.) However, other traditional manners of making antibodies, including monoclonal antibodies, using synthetic neoepitopes are also expressly contemplated herein.

In some embodiments where synthetic peptides (that comprise or correspond to the cancer neoepitope) is immobilized on a solid phase, affinity agents, and particularly antibodies to the neoepitope may be isolated and/or refined. Most preferably, such isolation will include a prefabricated high-diversity library of antibodies. As used herein, and unless the context dictates otherwise, the term "antibody" or "antibodies" includes all isotypes and subtypes of antibodies (e.g., IgG, IgM, IgE, etc.) as well as all fragments thereof, including monovalent IgG, F(ab')$_2$, Fab', Fab, scFv, scFv-Fc, VhH, etc. Moreover, contemplated antibodies may be humanized, of human or non-human (e.g., rodent) origin, or may be chimeric. In a typical method, a high-diversity library may be a phage display library having a diversity of at least $10^9$ diverse members, or at least $10^{10}$ diverse members, or even higher, typically based on M13 phages and display via pIII, pVIII, pVI, or pIX, or based on T7 phages and the gene 10 capsid protein. As should be readily appreciated, use of large diversity libraries will provide in relatively short time several binding candidate antibodies that can be further selected for best binders. Indeed, where binding affinity to the immobilized synthetic peptide is less than desired, it should be recognized that affinity can be improved via affinity maturation using protocols well known in the art. For example, low affinity ($K_D>10^{-7}M$) binders or members of smaller libraries may be subjected to affinity maturation to improve binding affinity and/or kinetic using methods well known in the art (see e.g., *Briefings In Functional Genomics And Proteomics*. Vol 1. No 2. 189-203. July 2002). In addition, it should be noted that while antibody libraries are generally preferred, other scaffolds are also deemed suitable and include beta barrels, ribosome display, cell surface display, etc. (see e.g., *Protein Sci.* 2006 January; 15(1): 14-27.) Thus, it should be appreciated that in preferred aspects the synthetic peptide is used as a bait in a library of antibodies to so identify high-affinity binding ($K_D<10^{-7}M$, and more typically $K_D<10^{-8}M$) antibodies.

As the antibodies are directly coupled to the cell that carries the nucleic acid encoding these antibodies, it should be further appreciated that such nucleic acid can then be analyzed to identify sequence elements encoding the hypervariable loops, the CDR1, CDR2, and CDR3, for light and heavy chain, respectively, and/or SDRs (specificity determining residues). Most typically, determination is performed using standard sequencing methods. Once determined, it is then contemplated that the hypervariable loops, or the CDR1-H, CDR2-H, and/or CDR3-H and/or the CDR1-L, CDR2-L, and/or CDR3-L, and/or SDRs are grafted onto a human or humanized antibody scaffold or antibody. As will be readily appreciated, grafting can be done by genetic engineering of a nucleic acid that encodes the human or humanized antibody scaffold or antibody. For example, within each CDR, there are more variable positions that are directly involved in the interaction with antigen, i.e., specificity-determining residues (SDRs), whereas there are more conserved residues that maintain the conformations of CDRs loops. SDRs may be identified from the 3D structure of the antigen-antibody complex and/or the mutational analysis of the CDRs. An SDR-grafted humanized antibody is constructed by grafting the SDRs and the residues maintaining the conformations of the CDRs onto human template. Consequently, it should be recognized that human or humanized antibodies with specificity to cancer neoepitopes can be prepared in an entirely synthetic manner in which the antibody is expressed in a cell that has not previously contacted the antigen. Moreover, contemplated methods allow production of patient and cancer specific antibodies for treatment of a patient that has failed to produce or effectively use antibodies against the neoepitopes.

While not limiting to the inventive subject matter, so prepared synthetic antibodies can be used directly as an IgG (or other isotype), as a fragment (e.g., bispecific Fab or other bispecific fragment), and/or as a chimeric protein (e.g., scFv as ectodomain in a chimeric T cell receptor), alone or in conjugation with a therapeutic or diagnostic agent, and/or as a hybrid protein with a transmembrane domain to ensure membrane anchoring of the antibody to a cell.

It is contemplated that the structure of synthetic peptides corresponding to or comprising the neoepitope sequences may be $X-L_1-(A_n-L_2)_m-Q$, in which X is an optional coupling group or moiety that is suitable to covalently or non-covalently attaches the synthetic peptide to a solid phase, $L_1$ is an optional linker that covalently links the synthetic peptide to a solid phase or the coupling group. $A_n$ is the synthetic peptide having the neoepitope sequence with A being a natural (proteinogenic) amino acid and n is an integer between 7 and 30, and most typically between 7 and 11 or 15-25. $L_2$ is an optional linker that may be present, especially where multiple synthetic peptide sequences (identical or different) are in the construct, and m is an integer, typically between 1 and 30, and most typically between 2 and 15. Finally, Q is a terminal group which may used to couple the end of the synthetic peptide to the solid phase (e.g., to sterically constrain the peptide) or to a reporter group (e.g., fluorescence marker) or other functional moiety (e.g., affinity marker). Consequently, it should be noted that where the synthetic peptide is used for direct MHC-I binding, the overall length will be between 8 and 10 amino acids. Similarly, where the synthetic peptide is used for direct MHC-II binding, the overall length will be between 14 and 20 amino acids. On the other hand, where the synthetic peptide is processed in the cell (typically via proteasome processing) prior to MHC presentation, the overall length will typically be between 10 and 40 amino acids, with the changed amino at or near a central position in the synthetic peptide.

For example, X could be a non-covalent affinity moiety (e.g., biotin) that binds a corresponding binding agent (e.g., avidin) on the solid phase, or a chemical group (with or without spacer) that reacts with the N- or C-terminal amino or carboxyl group of the peptide, or a selectively reactive group (e.g., iodoacetyl or maleimide group) that reacts with a sulfhydryl group in the peptide or linker $L_1$. $L_1$ may be used to increase the distance of the synthetic peptide from the solid phase and will therefore typically comprise a flexible linear moiety (e.g., comprising glycol groups, alkoxy groups, glycine, etc.) having a length of equivalent to between about 2-20 carbon-carbon bonds (e.g., between 0.3 nm and 3 nm). Of course, it should also be appreciated that the synthetic peptide may use the solid phase on which the peptide was produced and as such not require a separate coupling group or linker.

Depending on the particular synthetic peptide and coupling method, it should be appreciated that the nature of the solid phase may vary considerably, and all known solid phases for attachment of peptides are deemed suitable for use herein. For example, suitable solid phases include agarose beads, polymer beads (colored or otherwise individually addressable), wall surfaces of a well in a microtiter plate, paper, nitrocellulose, glass, etc. The person of ordinary skill in the art will be readily appraised of a suitable choice of solid phase and attachment chemistry. In further preferred aspects, it is also noted that the solid phase will generally be suitable for protocols associated with phage display methods such as to allow peptides presented on a phage (or other scaffold carrier) to reversibly bind to the solid phase via the synthetic peptide. In still further contemplated uses, it should also be recognized that the solid phase may be a carrier protein used in vaccination (e.g., albumin, KLH, tetanus toxoid, diphtheria toxin, etc.), particularly where the synthetic protein is used as a vaccine in a mammal or as an immunogenic compound in a non-human mammal for antibody production. Likewise, the synthetic protein may also be used as a vaccine or immunogenic compound without any carrier.

Regardless of the particular manner of identifying an antibody fragment or antibody that binds to the synthetic neoepitope, it should be appreciated that the displayed antibody fragment or antibody will provide via it's presenting structure (e.g., cell or phage) corresponding genetic information that lead to the production of the displayed antibody, and with that, information on the nucleotide sequences necessary to form the binding pocket. For example, where the displayed structure is an antibody fragment or antibody the nucleic acid sequence will provide sequence information for the complementarity determining regions CDR1, CDR2, and CDR3 domains of the light and heavy chains, respectively. This information can then be used to generate in vitro a nucleic acid sequence into which the sequence information for the CDR1, CDR2, and CDR3 domains of the light and heavy chains, respective, has been grafted. Transfection into a suitable system will then lead to the expression and production of a synthetic antibody ('synbody') with identical binding properties. Of course, it should be noted that the term antibody includes full-length antibodies as well as fragments/portions thereof.

A thusly produced antibody fragment or antibody may then be further modified to produce a therapeutic or diagnostic entity. For example, where the antibody fragment or antibody is labeled with a (e.g., PET or SPECT-active) isotope, the modified antibody fragment or antibody may be used for imaging. On the other hand, where the antibody fragment or antibody is labeled with a radionuclide or chemotherapeutic agent, the modified antibody fragment or antibody may be used for targeted chemotherapy. In still further contemplated aspects, the antibody fragment or antibody may also be modified with an antigen that is known to be an immunogenic antigen. Such modification is particularly advantageous where the patient was previously immunized with the same antigen. In such scenario, it is contemplated that the cancer cells with the neoepitopes are painted with the modified antibody presenting the immunogenic antigen, which is particularly advantageous where an immune response to the original neoepitope was not immunogenic or suppressed.

The applicants have further appreciated that the patient's bulk white blood cells (WBCs) can be cultured with the identified peptides (e.g., TAA, neoepitopes, etc.) by the inventive subject matter. Such an approach is expected to cause production of desired MHC/neoepitope complexes by the antigen presenting cells in the bulk WBCs. Thus, the patient's macrophages, dendritic cells, and B-Cells provide instruction to the NK cells and T-Cells so that they take on the desired properties to target the diseased tissue.

Yet another aspect of the inventive technology includes methods of detecting one or more features associated with T-Cells (e.g., CD4+ T-Cells, CD8+ T-Cells, etc.). More specifically, the tests can provide specific neoepitopes (e.g., 8-mers to 12-mers for MHC I, 12-mers to 25-mers for MHC II, etc.) that can be used for the identification of neoepitope reactive T-Cells bearing a specific T-Cell receptor against the neoepitopes/MHC protein complexes. Thus, the method can include harvesting the neoepitope reactive T-Cells. The harvested T-Cells can be grown or expanded ex vivo in preparation for reintroduction to the patient. Alternatively, the T-Cell receptor genes in the harvested T-Cells can be isolated and transferred into viruses, or other adoptive cell therapies systems (e.g., CAR-T, CAR-TANK, etc.). Beyond neoepitopes, methods of the inventive subject matter can also provide one or more tumor associated antigens (TAAs). Therefore one can also harvest T-Cells that have receptors that are sensitive to the TAAs identified from the test. These can also be grown or cultured ex vivo and used in a similar therapeutic manner as discussed above. The T-Cells can be identified by producing synthetic versions of the peptides and bind them with commercially produced MHC or MHC-like proteins, then using these ex vivo complexes to bind to the target T-Cells. One should appreciated that the harvested T-Cells can included T-Cells that have been activated by the patient's immune response to the disease, exhausted T-Cells, or other T-Cells that are responsive to the discussed features.

Viewed from another perspective, antibodies against neoepitopes may be used as targeting entities using NK cells, and especially NK-92 cells (that may be further modified to exhibit a high affinity Fc-cell receptor). Thus, in further contemplated aspects of the inventive subject matter, the antibody fragment or antibody may also be bound to a T-cell, and especially to a NK-cell to so stimulate and direct an immune response to the cells displaying the neoepitope. Consequently, it should be recognized that an effective immune response against a cancer neoepitope may be elicited using a process that does not require immunization in the patient or other organism, reducing dramatically response time and availability of therapeutic antibodies.

It is further contemplated that exhausted T-Cells can be reactivated through several different routes. One route includes using exogenously adding cytokines (e.g., IL-2, IL-12, IL-15, etc.) to the harvested exhausted T-Cells to reinvigorate the cells. The reinvigorated T-Cells can then be reintroduced back to the patient, possibly along with a checkpoint inhibitors (e.g., ipilimumab, etc.). Another route is to prevent exhaustion through blockading checkpoint inhibition, which can be achieved through administering a tailored virus having the target neoepitopes and with an appropriate inhibitor (e.g., LAG3, etc.).

EXAMPLE

As one example of methods of the inventive subject matter, a patient carrying HPV16 with cervical carcinoma was biopsied and the tissue sample was analyzed as described above. Non-patient reference sequences included HPV sequences, including HPV16 reference sequence. Notably, sequence analysis also revealed several mutations in the viral genome, leading to four neoepitopes. More specifically, four variants were found in the E6 gene and one variant in the E7 gene. In silico generation of a vaccine against the HPV16 virus using the virus reference sequence generated 242 possible epitopes across E6 and E7. The patient's omic sequence data were also used to predict HLA-types and results are shown in Table 1 below, and binding of the epitopes to the HLA-types was calculated as well as binding of the neoepitopes to the patient's HLA-types. This second calculation was then used to determine whether the variants in HPV16 significantly affect the epitopes that the patient was capable of binding.

| Allele 1 | Allele 2 [/ambiguous hit] |
|---|---|
| A*02:01 | A*68:01 |
| B*44:02 | B*44:02/B*44:03 |
| C*05:01 | C*16:01 |
| DRB1*04:01 | DRB1*07:01 |

-continued

| Allele 1 | Allele 2 [/ambiguous hit] |
|---|---|
| DQA1*03:03 | DQA1*02:01 |
| DQB1*03:01 | DQB*02:02 |
| E*01:01 | E*01:01 |
| G*01:01 | G*01:01 |
| H*01:01 | H*02:05 |
| DMA*01:01 | DMA*01:01/DMA*01:02 |
| DMB*01:03 | DMB*01:03/DMB*01:01 |
| DOA*01:01 | DOA*01:01 |
| DOB*01:01 | DOB*01:01/DOB*01:03 |
| DPA1*01:03 | DPA1*02:02 |
| DPB1*04:01 | DPB1*01:01 |
| DRA*01:01 | DRA*01:01 |

The table in FIG. 1 depicts exemplary results for binding epitopes and neoepitopes with respect to the predicted HLA-types, with predicted bound epitopes and neoepitopes highlighted. The first column (Entry) lists the identifier for some of the 242 possible epitopes and neoepitopes evaluated. The second column (Peptide) lists the amino acid sequence for the wildtype epitopes and neoepitopes across E6 and E7. The third through seventh columns (HLA-A02:01; HLA-A68:01; HLA-B44:02; HLA-B44:03; and HLA-005:01) list the predicted binding affinity in nM of the listed epitopes and neoepitopes for some of the patient's predicted HLA types. Of note, in this example epitopes and neoepitopes having high predicted binding affininty (<500 nM) are highlighted. The eighth column (Gene) identifies within which reference gene the epitopes and neoepitopes where identified, here the E6 gene and the E7 gene of HPV16. The ninth column (Variant Affected) identifies neoepitopes by amino acid sequence, where the neoepitope is a mutation of the wild type epitopes or neoepitopes from the second column.

Notably, Entry_70 is the only epitope depicted in FIG. 1 that is significantly altered by detected HPV16 Variants. Viewed from another perspective, methods of the inventive subject matter successfully identified a patient and virus specific neoepitope comprising mutations of the HPV16 sequence in the patient's genome, here a mutation of HPV16 reference amino acid sequence from KLPQLCTEL (SEQ. ID No. 6) to KLPDLCTEL (SEQ. ID No. 7).

FIG. 2 shows the predicted bound variant epitopes (neoepitopes) with high binding affinity for patient HLA type highlighted. It should be especially appreciated that a personalized HPV vaccine can be based on the HPV16 reference genome or based on a comparison of healthy tissue omics with diseased tissue omics would have been unable to target the two variant epitopes (neoepitopes) of FIG. 2. Viewed from another perspective, identification of the neoepitopes listed in FIG. 2 is not possible without comparison of viral reference genome with the viral sequence specifically integrated (and potentially subsequently mutated) in the patient's genome. Advantageously, the missense mutations leading to the neoepitopes in the patient were predicted to bind to at least one of the HLA types of the patient as listed in FIG. 2.

Specifically, as depicted in FIG. 2 neoepitope KLPDLCTEL results from a base change in the wild type E6 nucleic acid sequence from guanine to thymine, producing an amino acid change from wild type glutamine to mutant aspartic acid. Advantageously, neoepitope KLPDLCTEL has a very high predicted binding affinity for HLA-A02:01 of 12 nM. Further, neoepitope FQDPQERPI results from a base change in the wild type E6 nucleic acid sequence from guanine to thymine, producing an amino acid change from wild type arginine to mutant isoleucine. The FQDPQERPI neoepitope has a high predicted binding affinity for HLA-005:01 of 299 nM.

Thus, it should be recognized that vaccine efficacy can even be predicted in cases where viral DNA is subject to relatively high mutation rates and/or genomic instability by using methods of the inventive subject matter. As can also be taken from the data presented here, 18 total predicted epitopes were identified that would bind to patient's HLA type, while one epitope was no longer present due to generation of a non-binding variant and two neoepitopes were generated (and otherwise missed) due to these variants.

In yet another aspect of the inventive subject matter, and as already briefly addressed above, neoepitopes may also be calculated in silico and subsequently expressed from one or more recombinant nucleic acids in the affected tissue, wherein delivery of the nucleic acid is preferably performed in a gene and/or cell specific manner. For example, where the diseased tissue contains integrated viral DNA, that non-patient DNA can be specifically changed using adeno-viral vector delivery of RNA-guided CRISPR/Cas9 or CRISPR/Cpf1 nuclease complexes providing viral DNA with epitopes known or suspected to be immunogenic in the host (typically HLA-matched). Exemplary protocols for such delivery can be found in Nature, Scientific Reports 4, Article number: 5105 (2014). On the other hand, where the diseased tissue contains a mutated form of an oncogene or tumor suppressor gene, DNA can be delivered that introduces an immunogenic neoepitope to the cell.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a patient having a virus-associated tumor, comprising:
   obtaining a biopsy sample from the virus-associated tumor of the patient and analyzing the biopsy sample to identify a non-patient nucleic acid in the virus-associated tumor;
   determining a plurality of nucleic acid sequences encoding patient-specific and tumor-specific neoepitopes for the virus-associated tumor by identifying overlaps between the non-patient nucleic acid and a reference nucleic acid of a virus known to be related to the virus-associated tumor, wherein each of the neoepitopes has a length of between 5 and 30 amino acids, and wherein the non-patient nucleic acid includes a mutation compared to the reference nucleic acid of the virus related to the virus-associated tumor, and wherein the mutation occurs upon insertion of the non-patient nucleic acid into a patient's host genome;
   identifying an HLA-matched neoepitope from the plurality of patient-specific and tumor-specific neoepitopes, wherein the HLA-matched neoepitope includes the non-patient nucleic acid, includes the mutation, and has a dissociation constant equal to or less than 100 nM with an HLA-type of the patient; and
   administering to the patient having the virus-associated tumor an immunotherapeutic composition comprising a recombinant virus that includes the nucleic acid encoding the HLA-matched neoepitope or a recombinant cell expressing a recombinant protein that targets the HLA-matched neoepitope, thereby triggering an immune response against the HLA-matched neoepitope of the virus-associated tumor.

2. The method of claim 1 wherein identifying the non-patient nucleic acid further comprises matching omics data of the virus-associated tumor tissue of the patient against a healthy tissue of the same patient.

3. The method of claim 1 wherein the non-patient nucleic acid is a portion of a genome of the virus.

4. The method of claim 1 wherein the plurality of neoepitopes are generated for a gene expressed in the virus-associated tumor tissue of the patient.

5. The method of claim 1 wherein the reference nucleic acid includes a plurality of nucleic acid sequences of known HLA types.

6. The method of claim 1 wherein the nucleic acid encoding the HLA-matched neoepitope includes a nucleic acid fragment encoding a targeting peptide that directs a neoepitope matched with an MHC-II subtype HLA for an MHC-II presentation pathway.

7. The method of claim 1 wherein the recombinant virus includes a recombinant nucleic acid encoding the HLA-matched neoepitope as a multimer.

8. A method of making a patient-specific immunotherapeutic composition for treating a patient having a virus-associated tumor, comprising:
   obtaining a biopsy sample from the virus-associated tumor of the patient and analyzing the biopsy sample to identify a non-patient nucleic acid in the virus-associated tumor;
   determining a plurality of nucleic acid sequences encoding epitopes and a neoepitope having a length of between 5 and 30 amino acids by identifying overlaps between the non-patient nucleic acid and a reference nucleic acid of a virus known to be related to the virus-associated tumor, wherein the non-patient nucleic acid includes a mutation, wherein the mutation occurs upon insertion of the non-patient nucleic acid into a patient's host genome;
   identifying an HLA-matched neoepitope from the plurality of patient-specific and tumor-specific neoepitopes, wherein the HLA-matched neoepitope includes the non-patient nucleic acid, includes the mutation, and has a dissociation constant equal to or less than 100 nM with an HLA-type of the patient; and
   making the patient-specific immunotherapeutic composition comprising a recombinant virus that includes a nucleic acid fragment encoding the HLA-matched neoepitope, or a recombinant cell expressing a recombinant protein that targets the HLA-matched neoepitope.

9. The method of claim 8 wherein identifying the non-patient nucleic acid further comprises matching omics data of the virus-associated tumor tissue of the patient against a healthy tissue of the same patient.

10. The method of claim 8 wherein the virus integrates at least a portion of the virus genome into the patient's genome.

11. The method of claim 8 wherein the plurality of epitopes for the reference nucleic acid are calculated for at least one gene expressed by the virus.

12. The method of claim 8 further comprising a step of determining in silico an HLA-type of the virus-associated tumor tissue of the patient.

13. The method of claim 8 wherein the nucleic acid encoding the HLA-matched neoepitope includes a nucleic acid fragment encoding a targeting peptide that directs a neoepitope matched with an MHC-II subtype HLA for an MHC-II presentation pathway.

14. A method of using omics data from a patient having a virus-associated tumor that includes a patient-specific and tumor-specific mutation, comprising:
   obtaining a biopsy sample from the virus-associated tumor of the patient and analyzing the biopsy sample to identify a non-patient nucleic acid in the virus-associated tumor;

determining a plurality of nucleic acid sequences encoding patient-specific and tumor-specific neoepitopes having a length of between 5 and 30 amino acids by identifying overlaps between the non-patient nucleic acid and a reference nucleic acid of a virus related to a virus-associated tumor, wherein the non-patient nucleic acid includes a mutation generated upon insertion of the non-patient nucleic acid into a patient's host genome;

identifying an HLA-matched neoepitope from the plurality of patient-specific and tumor-specific neoepitopes, wherein the HLA-matched neoepitope includes the non-patient nucleic acid, includes the mutation, and has a dissociation constant equal to or less than 100 nM with an HLA-type of the patient; and making a nucleic acid construct comprising a nucleic acid encoding an HLA-matched neoepitope having the non-patient nucleic acid that includes the mutation wherein the mutation occurs upon insertion of the non-patient nucleic acid into a patient's host genome, and wherein the HLA-matched neoepitope is one of the plurality of neoepitopes having a calculated dissociation constant of equal to or less than 100 nM.

15. The method of claim 14 wherein the plurality of neoepitopes are generated for a gene expressed by the virus-associated tumor tissue of the patient.

16. The method of claim 14 wherein the nucleic acid construct comprises a CRISPR/Cas9 cassette.

17. The method of claim 16 wherein the nucleic acid construct further comprises a guide RNA that is specific to the non-patient nucleic acid.

* * * * *

SEQUENCE LISTING

```
<160> NUMBER OF SEQ ID NOS: 25

<210> SEQ ID NO 1
<211> LENGTH: 9
<212> TYPE: PRT
<213> ORGANISM: Homo sapiens

<400> SEQUENCE: 1

Thr Leu His Glu Tyr Met Leu Asp Leu
1               5

<210> SEQ ID NO 2
<211> LENGTH: 9
<212> TYPE: PRT
<213> ORGANISM: Homo sapiens

<400> SEQUENCE: 2

Tyr Asn Ile Val Thr Phe Cys Cys Lys
1               5

<210> SEQ ID NO 3
<211> LENGTH: 9
```

```
<212> TYPE: PRT
<213> ORGANISM: Homo sapiens

<400> SEQUENCE: 3

Cys Met Ser Cys Cys Arg Ser Ser Arg
1               5

<210> SEQ ID NO 4
<211> LENGTH: 9
<212> TYPE: PRT
<213> ORGANISM: Homo sapiens

<400> SEQUENCE: 4

Gly Thr Leu Gly Ile Val Cys Pro Ile
1               5

<210> SEQ ID NO 5
<211> LENGTH: 9
<212> TYPE: PRT
<213> ORGANISM: Homo sapiens

<400> SEQUENCE: 5

Tyr Met Leu Asp Leu Gln Pro Glu Thr
1               5

<210> SEQ ID NO 6
<211> LENGTH: 9
<212> TYPE: PRT
<213> ORGANISM: Homo sapiens

<400> SEQUENCE: 6

Lys Leu Pro Gln Leu Cys Thr Glu Leu
1               5

<210> SEQ ID NO 7
<211> LENGTH: 9
<212> TYPE: PRT
<213> ORGANISM: Homo sapiens

<400> SEQUENCE: 7

Lys Leu Pro Asp Leu Cys Thr Glu Leu
1               5

<210> SEQ ID NO 8
<211> LENGTH: 9
<212> TYPE: PRT
<213> ORGANISM: Homo sapiens

<400> SEQUENCE: 8

Phe Tyr Ser Lys Ile Ser Glu Tyr Arg
1               5

<210> SEQ ID NO 9
<211> LENGTH: 9
<212> TYPE: PRT
<213> ORGANISM: Homo sapiens

<400> SEQUENCE: 9

Glu Val Tyr Asp Phe Ala Phe Arg Asp
1               5

<210> SEQ ID NO 10
<211> LENGTH: 9
<212> TYPE: PRT
<213> ORGANISM: Homo sapiens
```

<400> SEQUENCE: 10

Leu Ile Arg Cys Ile Asn Cys Gln Lys
1               5

<210> SEQ ID NO 11
<211> LENGTH: 9
<212> TYPE: PRT
<213> ORGANISM: Homo sapiens

<400> SEQUENCE: 11

Leu Leu Met Gly Thr Leu Gly Ile Val
1               5

<210> SEQ ID NO 12
<211> LENGTH: 9
<212> TYPE: PRT
<213> ORGANISM: Homo sapiens

<400> SEQUENCE: 12

Ile Val Cys Pro Ile Cys Ser Gln Lys
1               5

<210> SEQ ID NO 13
<211> LENGTH: 9
<212> TYPE: PRT
<213> ORGANISM: Homo sapiens

<400> SEQUENCE: 13

Gln Ala Glu Pro Asp Arg Ala His Tyr
1               5

<210> SEQ ID NO 14
<211> LENGTH: 9
<212> TYPE: PRT
<213> ORGANISM: Homo sapiens

<400> SEQUENCE: 14

Glu Thr Thr Asp Leu Tyr Cys Tyr Glu
1               5

<210> SEQ ID NO 15
<211> LENGTH: 9
<212> TYPE: PRT
<213> ORGANISM: Homo sapiens

<400> SEQUENCE: 15

Ile Ile Leu Glu Cys Val Tyr Cys Lys
1               5

<210> SEQ ID NO 16
<211> LENGTH: 9
<212> TYPE: PRT
<213> ORGANISM: Homo sapiens

<400> SEQUENCE: 16

Phe Ala Phe Arg Asp Leu Cys Ile Val
1               5

<210> SEQ ID NO 17
<211> LENGTH: 9
<212> TYPE: PRT
<213> ORGANISM: Homo sapiens

<400> SEQUENCE: 17

Tyr Ala Val Cys Asp Lys Cys Leu Lys
1               5

<210> SEQ ID NO 18
<211> LENGTH: 9
<212> TYPE: PRT
<213> ORGANISM: Homo sapiens

<400> SEQUENCE: 18

Thr Thr Leu Glu Gln Gln Tyr Asn Lys
1               5

<210> SEQ ID NO 19
<211> LENGTH: 9
<212> TYPE: PRT
<213> ORGANISM: Homo sapiens

<400> SEQUENCE: 19

Val Cys Asp Lys Cys Leu Lys Phe Tyr
1               5

<210> SEQ ID NO 20
<211> LENGTH: 9
<212> TYPE: PRT
<213> ORGANISM: Homo sapiens

<400> SEQUENCE: 20

Lys Leu Pro Asp Leu Cys Thr Glu Leu
1               5

<210> SEQ ID NO 21
<211> LENGTH: 9
<212> TYPE: PRT
<213> ORGANISM: Homo sapiens

<400> SEQUENCE: 21

Lys Leu Pro Gln Leu Cys Thr Glu Leu
1               5

<210> SEQ ID NO 22
<211> LENGTH: 9
<212> TYPE: PRT
<213> ORGANISM: Homo sapiens

<400> SEQUENCE: 22

Phe Gln Asp Pro Gln Glu Arg Pro Ile
1               5

<210> SEQ ID NO 23
<211> LENGTH: 9
<212> TYPE: PRT
<213> ORGANISM: Homo sapiens

<400> SEQUENCE: 23

Phe Gln Asp Pro Gln Glu Arg Pro Arg
1               5

<210> SEQ ID NO 24
<211> LENGTH: 9
<212> TYPE: PRT
<213> ORGANISM: Homo sapiens

<400> SEQUENCE: 24

Trp Ile Arg Met Lys Thr Gly Asn Lys

```
<210> SEQ ID NO 25
<211> LENGTH: 9
<212> TYPE: PRT
<213> ORGANISM: Homo sapiens

<400> SEQUENCE: 25

Trp Ile Arg Lys Lys Thr Gly Asn Lys
1               5
```